(12) United States Patent
Ziv

(10) Patent No.: US 7,169,940 B1
(45) Date of Patent: Jan. 30, 2007

(54) COMPOUNDS AND PHARMACEUTICAL COMPOSITIONS COMPRISING SAME

(75) Inventor: Ilan Ziv, Kfar Sava (IL)

(73) Assignee: NST Neurosurvival Technologies Ltd., Petach Tikva (IL)

( * ) Notice: Subject to any disclaimer, the term of this patent is extended or adjusted under 35 U.S.C. 154(b) by 602 days.

(21) Appl. No.: 10/129,145

(22) PCT Filed: Oct. 31, 2000

(86) PCT No.: PCT/IL00/00699

§ 371 (c)(1),
(2), (4) Date: May 2, 2002

(87) PCT Pub. No.: WO01/32662

PCT Pub. Date: May 10, 2001

(30) Foreign Application Priority Data

Nov. 2, 1999 (IL) .................................. 132705
Jul. 3, 2000 (IL) .................................. 137148

(51) Int. Cl.
*C07D 493/10* (2006.01)
*A61K 31/357* (2006.01)

(52) U.S. Cl. ............ 549/341; 549/334; 549/342; 549/343; 514/452; 514/462

(58) Field of Classification Search ............ 549/334, 549/341, 342, 343; 514/452, 462
See application file for complete search history.

(56) References Cited

U.S. PATENT DOCUMENTS 5,883,235 A   3/1999   Byrnard et al.

FOREIGN PATENT DOCUMENTS

WO   WO 99 19470 A   4/1999

OTHER PUBLICATIONS

Shimada et al. "Elaeodendroside D, E, H, I . . . " CA 94:157182 (1981).*
Ziv "Preparation of Ca2+ binding compounds" CA 134:353475 (2001).*

* cited by examiner

*Primary Examiner*—Celia Chang
(74) *Attorney, Agent, or Firm*—Browdy and Neimark, PLLC

(57) ABSTRACT

NST 400 compounds consisting of a unit for partial coordination of Ca2+ ions (CPCU). The NST 400 compounds are optionally conjugated to another pharmaceutically active compound. The compounds and conjugates can be used for affinity filters and for binding negative charged phospholipids. The compounds and conjugates can also be used for treating diseases involving changes of cell membrane asymmetry.

Figure 1:
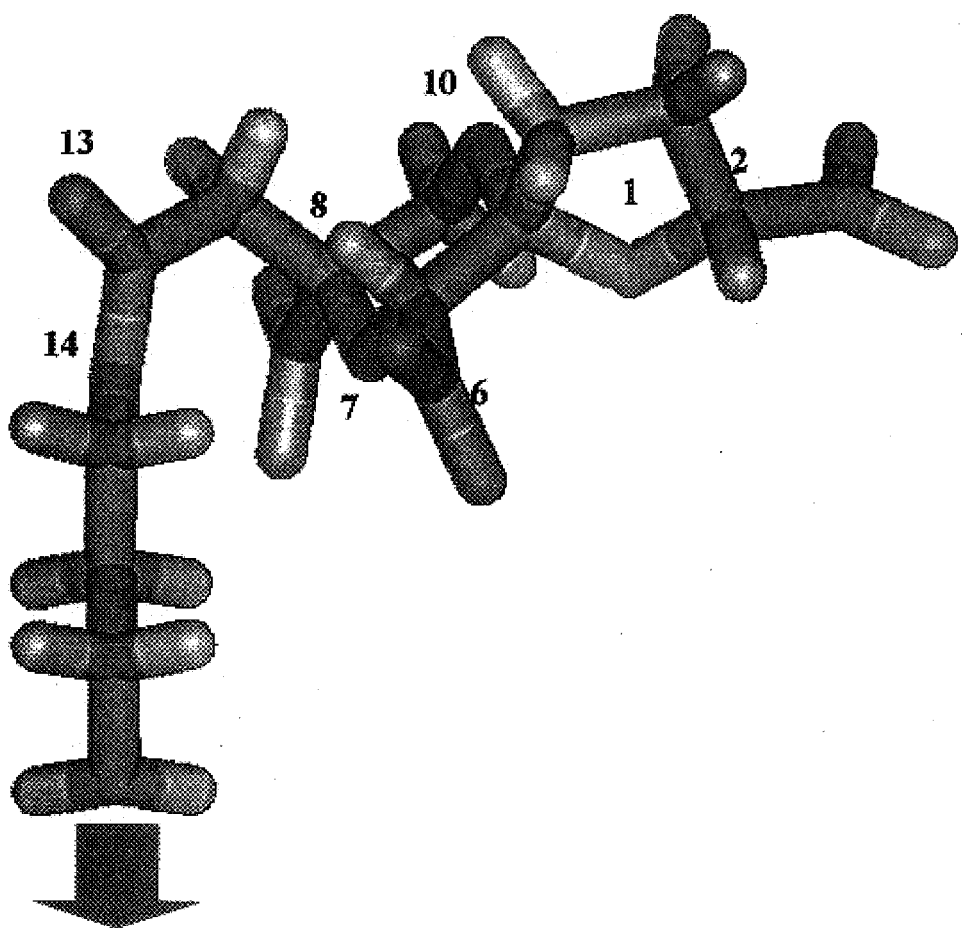

4 Claims, 4 Drawing Sheets
(4 of 4 Drawing Sheet(s) Filed in Color)

$C_{14}H_{29}$

COMPOUNDS AND PHARMACEUTICAL COMPOSITIONS COMPRISING SAME

The present invention relates to novel compounds and pharmaceutical preparations comprising same, and to novel methods, their use in the binding to negative-charged phospholipids (NCP), and their use for the diagnosis and treatment of certain diseases, in particular of diseases involving changes of cell membrane lipid asymmetry (CMLA).

Biological membranes are composed of several phospholipids that have a net negative charge at physiological pH. Phosphatidylserine (PS) is the major NCP. Therefore, this invention focuses on PS, while not being limited to it, i.e., the compounds of the present invention may be also useful for binding to other NCP's, such as phosphatidic acid, phosphatidylglycerol, phosphatidylinositol and cardiolipin. Similarly, while the current invention focuses on the NCP's being part of a cell membrane, said NCP may be incorporated in other phospholipid containing structures, such as liposomes, micelles or phospholipid-coated surfaces.

Phosphatidylserine (PS) is an aminophospholipid, which has a net charge of (−1) at physiological pH. In recent years, phospholipid membranes containing a certain amount of PS (herein designated PSM for Phosphatidylserine in biological Membranes) have been shown to constitute binding sites for various proteins. These proteins include, among others, Src, protein kinase C (PKC), CD11, synaptotagmin, annexins and several coagulation factors. While these proteins have diverse functions, they all share binding to PSM. A compound, capable of binding to PSM is hereby designated PSM ligand or PSML. Normally, PS is asymmetrically distributed between the leaflets of the phospholipid membrane bilayer, being concentrated in the inner leaflet, where its levels may reach 33% of total phospholipids. This phenomenon, hereby designated cell membrane lipid asymmetry (CMLA), is shared by almost all eukaryotic cells (Zwaal R F A & Schronit A J, Blood 1997; 89:1121–1132). The physiological importance of CMLA is exemplified by the fact that its maintenance requires a continuous, considerable investment of energy by the cell (Seigneuret M & Devaux P F, Proc. Natl. Acd. Sci., 1984; 81:3751).

While maintenance of CMLA is fundamental to normal cell physiology, its loss, with subsequent surface exposure of PS plays a role in numerous physiological and pathological states. Such process causes the outer leaflet of the cell membrane to be of negative-charge, while concomitantly reducing the level of packing of its phospholipid molecules. These alterations play an indispensable role in the formation of a catalytic surface for the assembly of several clotting factor complexes, e.g., tenase and prothrombinase complexes. Thus, loss of CMLA in activated platelets as well as in other cell types (e.g. endothelial cells), is an important factor in normal blood coagulation. However, CMLA loss may also assist in the initiation and/or propagation of abnormal, excessive blood clotting in numerous disorders. These disorders include, among others:

1. Arterial or venous thrombosis (Thiagarajan P & Benedict C R, Circulation 1997; 96:2339–2347; Van Ryn McKenna J, et al., Throm. Hemost. 1993; 69:227–230).

2. Sickle cell disease (Tait J F & Gibson D, J. Lab. Clin. Med. 1994; 123:741).

3. Beta-thalassemia (Borenstein-Ben-Yashar Y, et al., Am. J. Hematol. 1994; 47:295; Ruf A, et al., Br. J. Haematol. 1997; 98:51–56).

4. Antiphospholipid antibody syndrome; among others in systemic lupus erythematosus. Lack of CMLA has been specifically linked to the recurrent abortions associated with said syndrome (Rand J H, et al., N. Engl. J. Med. 1997; 337:154–160).

5. Disorders associated with shedding of membrane microparticles, e.g., during cardiopulmonary bypass, (Nieuwland R et al., Circulation 1997; 96:3534–3541; Aupeix K, et al., J. Clin. Invest. 1997; 99:1546–155). Said microparticles originate from damaged or senescent blood or endothelial cells, activated platelets, or cells undergoing apoptosis.

Urolithiasis is another disease process in which there is evidence for a role for surface exposure of PS. Said PS assists in calcium oxalate crystal formation and attachment to epithelial cells, thus promoting stone formation (Lieske J C, et al., Am. J. Physiol. 1996; 270:F192–F199; Bigelow M W, et al., Am. J. Physiol. 1997; 272: F55–F62).

Apoptosis is another major situation in which CMLA loss takes place. Apoptosis is an intrinsic program of cell self-destruction or "suicide", which is inherent in every eukaryotic cell. In response to a triggering stimulus, cells undergo a highly characteristic cascade of events of cell shrinkage, blebbing of cell membranes, chromatin condensation and fragmentation, culminating in cell conversion to clusters of membrane-bound particles (apoptotic bodies), which are thereafter engulfed by macrophages (Boobis A R, et al., Trends Pharmacol. Sci. 10:275–280, 1989; Bursch W, et al., Trends Pharmacol. Sci. 13:245–251, 1992). Loss of CMLA is a universal phenomenon in apoptosis (Van den Eijnde S M, et al., Cell death Diff. 1997; 4:311–316), it occurs early in the apoptotic cascade, probably at the point of cell commitment to the death process (Van-Engeland M, et al., Cytometry 1998; 31:1–9; Martin S J, et al., J. Exp. Med. 1995; 182:1545–1556), and has also been shown to be an important factor in the recognition and removal of apoptotic cells by macrophages (Balasubramanian K, et al., J. Biol. Chem. 1997; 272:31113–31117). A strong correlation has recently been drawn between loss of CMLA and potent procoagulant activity of apoptotic cells (Bombeli T, et al., Blood 1997; 89:2429–2442; Flynn P D, et al., Blood 1997; 89:4378–4384). CMLA loss in apoptotic endothelial cells, such as in atherosclerotic plaques (Kockx M M, et al., Circulation 1998; 97:2307–2315, Mallat Z, et al., Circulation 1997; 96:424–428), probably plays an important role in the pathogenesis of thrombotic vascular disorders.

The diagnosis of loss of CMLA may therefore serve as an important tool for the detection of cell death, specifically by apoptosis. A method for detection of cell death may have many applications, both as a diagnostic tool and as a method to monitor disease course in numerous disorders. These include, among others:

1. Monitoring of response to anti-cancer therapy: Currently there is a lag period between the time of administration of anticancer drugs and the time of evaluation of their efficacy. In case of failure of a therapeutic regimen, this lag time may lead to an untoward loss of precious time without an effective therapy, while subjecting the patient to unnecessary exposure to adverse effects commonly associated with these drugs. Therefore, there is clearly a need for better tools for early detection of tumor response to treatment. Since most anti-tumor drugs exert their effects by induction of apoptosis (Eastman A, Cancer Cells, 1990; 2:275–280), detection of apoptosis, potentially by detection of CMLA loss may be useful for monitoring of tumor response to treatment.

2. Diagnosis of disorders of inappropriate excessive apoptosis: These disorders include, among others, AIDS, neurodegenerative disorders, myelodysplastic syndromes and various ischemic or toxic insults (Thompson C B, Science 1995; 267:1456–1461).

3. Monitoring of graft survival following organ transplantation: The increasing use of organ transplantation for the treatment of end-stage organ failure emphasizes the need for the development of methods for sensitive monitoring of graft survival. Apoptosis plays a major role in graft cell loss (Matsuno T, et al., Transplant Proc. 1996; 28:1226–1227; Dong C et al., Lab. Invest. 1996; 74:921–931).

4. Monitoring of response to cytoprotective treatments: The current intensive research of cytoprotective agents, towards development of drugs capable of inhibiting cell loss in various diseases (Thompson C B, Science 1995; 267: 1456–1461), dictates a need for measures to evaluate the effects of such compounds, i.e., monitoring of cell death, in all levels of research, from in vitro tissue culture studies, through in vivo animal models to human clinical studies.

5. Basic research of apoptosis in tissue cultures and animal models.

These considerations therefore demonstrate the potential importance of PSML in various physiological and pathophysiological states. Said ligand may therefore have wide diagnostic applications, e.g., by marking apoptotic cells. Moreover, by shielding the exposed NCP, such compound may be a useful therapeutic agent in various diseases, that include, among others, the above-mentioned procoagulant states or urolithiasis.

PSM ligand (PSML), may also have important applications for targeting drugs to tissues inflicted by CMLA loss, e.g., apoptotic or thrombotic tissues. The implementation of the emerging new generation of drugs, acting on the apoptotic control machinery is expected to depend, at least in part, on the ability to target these drugs to the appropriate tissues. Since apoptosis is shared by all tissues in the body, it is highly undesirable to cause a non-differential alterations in its threshold. Therefore, a PSML may therefore be useful for this differenetial targeting task.

Equally important is the targeting of antithrombotic or fibrinolytic drugs to regions of thrombus formation, causing cerebral stroke or myocardial infarction. Current therapy with agents such as heparin or tissue plasminogen activator (tPA), respectively, is sometimes associated with the complication of bleeding (Katzan I L, et al., JAMA 2000; 283:1151–1158; Albers G W, et al., JAMA 2000; 283: 1145–1150) due, at least in part, to the systemic effect exerted by these agents. It is therefore highly desirable to have a pharmacological tool, capable of targeting the antithrombotic or fibrinolytic treatment to the thrombus region. Since one of the hallmarks of such region is high load of CMLA-loss elements, such as activated platelets and damaged/apoptotic endothelial cells, PSML, by binding to these elements may be suitable for this task.

Currently, the only known naturally-occurring high-affinity PSMLs are proteins. Their use as drugs or as diagnostic probes is often limited by several inherent properties of proteins, such as rapid degradation and inactivation, potential immunogenity, and size-based limitation of biodistribution. Several of these problems have been solved in the novel PSML's NST300 and NST500 compounds [co-pending Israeli patent applications Nos. 125908 (NST 300 compounds); and 131266 (NST 500 compounds)]. However, there should still be found novel PSMLs, being of non-protein structure; thus avoiding the inherent limitations of proteins as drug candidates.

The present invention thus relates to a novel class of PSMLs.

The present invention thus consists in a component comprising a unit for partial coordination of $Ca^{2+}$ ions (hereinafter called "CPCU") and a hydrophobic residue, which CPCU unit has a molecular weight of less that 2,000 daltons, has at least one $Ca^{2+}$ binding sites (CBSs) thus forming $CPCU.Ca^{2+}_n$ complex (n stands for the number of CBSs within the CPCU), each CBS meeting the following conditions:

a. It provides at least three electronegative atoms, at the proper three-dimensional orientation for the coordination of a $Ca^{2+}$ ion;

b. after binding of $Ca^{2+}$ to a binding site (CBS), the $Ca^{2+}$ ion still has one or more coordination sites that are unoccupied; and c. the electronegative atoms of the CBS, coordinating the $Ca^{2+}$ ion (hereinafter; "coordinating atoms" or CA) are individually selected among oxygen, nitrogen, sulfur and fluorine; and the hydrophobic residue consists in $A_b$ groups in which b stands for an integer of 1–3, A stands for a hydrophobic moiety, and is selected among:

a) linear or branched $C_3$–$C_{20}$ alkyl, linear or branched $C_2$–$C_{20}$ alkenyl, cycloalkyl or cycloalkenyl;

b) aryl or indole group;

c) saturated or unsaturated fatty acid of 3–20 carbon atoms;

d) amino acid residue, selected among alanine, valine, leucine, isoleucine, phenylalanine, tryptophan and tyrosine;

e) intra- or inter-group combinations of members of (a) and/or (b); or members of groups (b) and/or (c);

f) hydrophobic moiety having preference of binding to loosely-packed membranes; such moiety having a bulky structure and is of molecular weight greater than 200; and wherein CPCU unit and the hydrophobic residue are connected via linker L in which L is either 0 or selected among linear or branched $C_1$–$C_6$ alkyl; linear or branched $C_2$–$C_6$ alkenyl; $C_3$–$C_6$ cycloalkyl; $C_3$–$C_6$ cycloalkenyl; and a combination of any of said alkyl and/or alkenyl and/or cycloalkyl and or cycloalkenyl.

The net formal charge of the $CPCU.Ca^{2+}_n$ complex (when CPCU is being a part of the NST compound as defined hereinafter) is either neutral or positive.

In case that CA is an oxygen atom, CA is part of a chemical group or part of a residue, being or comprising any of the following: carboxyl, carboxylate, carboxylic acid, phosphate, phosphoric acid, sulfate, sulfuric acid, phosphonate, phosphonic acid, sulfonate, sulfonic acid, aldehyde, ketone, ester, amide, anhydride, hydroxyl, hydroxylamine or ether, [hereinafter "coordinating atom-bearing group" (CABG)].

Advantageously, the CBSs within the CPCU share one or more CAs, or share one or more CABG; Said "sharing" herein means that in said CPCU, one or more CAs or one or more CABGs can concomitantly coordinate more than one $Ca^{2+}$ ion.

In a preferred embodiment the CPCU has general formula I:

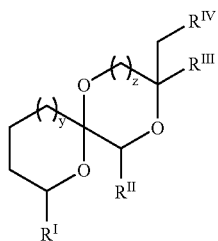

wherein y and z stand each for an integer of 0 or 1; $R^I$, $R^{III}$ and $R^{IV}$ stand each for a CABG, as hereinbefore defined; $CH2-R^{IV}$ may be replaced by H; and $R^{II}$ comprises a chemical group selected among carboxyl, sulfate and phosphate; preferably, $R^I$, $R^{II}$, $R^{III}$ and $R^{IV}$ each comprises a chemical group selected among carboxylic acid, ester, amide or ketone.

In a preferred embodiment, $R^I$, $R^{II}$, $R^{III}$ and $R^{IV}$ all comprise carboxyl groups, in which case the CPCU is designated M-CPCU.

NST 400 compounds are herein defined to consist of the component as herein defined being connected to groups $B_d$ and $D_e$ via linker L in which B stands for an amine or an acid addition salt thereof; D stands for a functional group selected among amine, carboxyl, hydroxyl, thiol and aldehyde; d stands for an integer of 0–6, e stands for an integer of 0–3 and L is as hereinbefore defined.

NST 400 compounds may be either in acid form or pharmaceutically acceptable salts and chelate complexes thereof, since physiological conditions (mainly pH, ionic strength and extracellular $Ca^{2++}$ concentrations) allow their activity in either form.

In a preferred embodiment the CABGs of the CPCU in the NST400 compound comprise any of the following: carboxyl, carboxylate, phosphate, sulfate, phosphonate and sulfonate, and wherein the NST 400 compound is in acid form or a pharmaceutically-acceptable salts and chelate complexes thereof.

Said NST400 compound may be connected to one or two A residues, either directly or via a L residue.

A may be selected from a group consisting of: a linear hydrocarbon chain of 8–20 carbon atons; residues of myristic acid, farnesol; indole;

phenylalanine; tyrosine; tryptophan;

N-E-(5-dimethylaminonaphthalene-1-sulfonyl) and analogues thereof; and a chemical group comprising a steroid ring system.

L stands for a linker, linking CPCU, A and B and D residues if present (as hereinafter defined) within the NST400 compound.

L is preferably selected from:
1). Linear or branched $C_1$–$C_6$ alkyl;
2). Linear or branched $C_2$–$C_6$ alkenyl;
3). $C_3$–$C_6$ cycloalkyl;
4). $C_3$–$C_6$ cycloalkenyl;
5). Any combination of members of groups (1), (2), (3) and (4).

CPCU, A, L and B residues may each also comprise a functional group, suitable for linkage of the residue to the other components of the NST400 compound through an etheric, esteric, ketone or amide bond.

Individual A, L or B units in a NST 400 compound may be structurally identical or non-identical to other A, L, or B units, respectively, comprising the compound.

The NST 400 compounds may also comprise an additional residue D, which may be bound to CPCU, A, L or B. D stands for a functional group, selected among amine, carboxyl, hydroxyl, thiol and aldehyde.

D serves to link the NST400 compound to any of the following:
1). Solid support;
2). Marker for imaging, e.g. detectors of fluorescence, x-ray, magnetic resonance imaging (MRI), or radio-isotope scan;
3). Another drug, to be targeted via linkage to the NST400 compound. Preferably the drug may be an inhibitor of apoptosis, (e.g., caspase inhibitor, antioxidant) or a cytotoxic agent, such as an activator of apoptosis (e.g., anticancer drugs); alternatively, the drug is preferably an antithrombotic or a fibrinolytic agent selected among heparin, low molecular weight heparin, antagonists of glycoprotein IIb/IIIa and tissue plasminogen activator (tPA).

A NST400 compound, having CPCU of general formula I is defined as NST401 compound. Preferably, CPCU of the NST400 compound is M-CPCU, as defined hereinbefore.

In a preferred embodiment, NST 401 compound has general formula II:

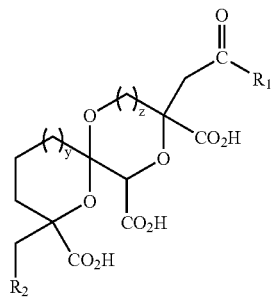

wherein y and z stand each for an integer of 0 or 1; and wherein either $R_1$ or $R_2$ stands for A or L—A; the other moiety (either $R_1$ or $R_2$) stands for a group selected among H; A; L—A; B; L—B; D; L—D; L; or $R_1$ stands for —OH; or $R_2$ stands for —$CO_2H$;

A, B and L are as hereinbefore defined.

In a specific embodiment, $R_1$ is V—A or V—$C_{14}H_{29}$; wherein V is selected among —N(H)— and —O—; and $R_2$ is selected among —H and —L—D. In the case that $R_1$ is —A and $R_2$ is H, the NST 401 compound has general formula III:

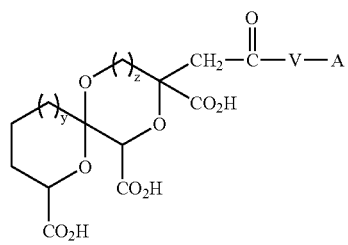

y and z having the same meanings as above.

When y=z=1; $R_1$=V—$C_{14}H_{29}$; wherein V=—O—; $R_2$=H; the compound is designated NST401-A.

When y=0; z=1; $R_1$=V—$C_{14}H_{29}$; wherein V=—O—; $R_2$=H; the compound is designated NST401-B.

When y=z=1; $R_1$=V—$C_{14}H_{29}$; wherein V=—N(H)—; $R_2$=H; the compound is designated NST401-C.

When y=0; z=1; $R_1$=V—$C_{14}H_{29}$; wherein V=—N(H)—; $R_2$=H; the compound is designated NST401-D.

The preferred stereo-isomer of NST401-D has general formula IV:

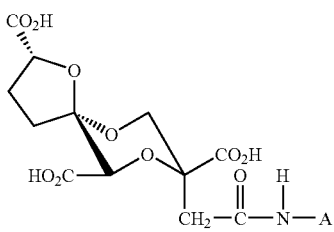

In yet another embodiment, NST401 compound has general formula V:

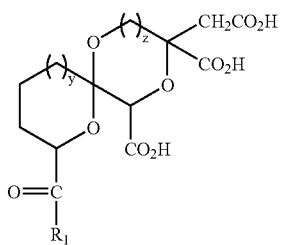

y, z and $R_1$ having the same meanings as above.

When y=0; z=1; and $R_1$=O—$C_{14}H_{29}$; the compound is designated NST401-E.

The preferred stereo-isomer of NST401-E has general formula VI:

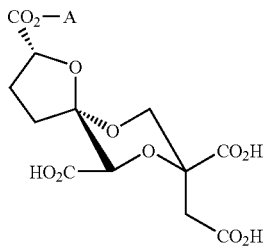

The present invention also concerns a conjugate of NST400 compound and another pharmaceutically active compound, the conjugate is designated "T-NST400 conjugate". Said conjugation is performed via moiety D of the NST400 compound, as defined hereinbefore. Preferably, the active compound to be conjugated to NST400 is selected among:

1). Marker for imaging, e.g. detectors of fluorescence, x-ray, magnetic resonance imaging (MRI), or radio-isotope scan;
2). A drug to be targeted to specific tissues, wherein CMLA loss takes place. Preferably, the drug is a modulator of apoptosis, being either an apoptosis inhibitor (e.g., caspase inhibitor or an antioxidant) to be targeted to tissues of abnormally excessive apoptosis; or a cytotoxic drug, preferably an apoptosis inducer, to be targeted to tissues where augmentation of apoptosis is warranted, such as cancerous tissues undergoing therapy.
3). Antithrombotic or fibrinolytic agent, selected among heparin, low molecular weight heparin, antagonists of glycoprotein IIb/IIIa and tissue plasminogen activator (tPA).

NST401 compounds utilize the mechanism of action of the NST400 compounds in binding to PSM, as exemplified by NST401-B (Examples 1, 2; FIGS. 1–4). It contains two CBS's, each providing 4 oxygen atoms to coordinate a $Ca^{2+}$ ion. Three-dimensional orientation of said coordinating atoms being in a good fit to four vertices of the pentagonal bipyramid, with an average $Ca^{2+}$—CA distance of 2.4 Å, characteristic of the coordination geometry of $Ca^{2+}$ (McPhalen C A, e al., Adv Prot Chem 1991; 12:77–143), [root mean square deviation (RMSD) of 0.37–0.41]. One of the carboxyl groups coordinates both $Ca^{2+}$ ions (sharing of CABG, as specified above). Overall charge of NST401-B upon binding of the two $Ca^{2+}$ ions is +1. Since the most frequent coordination number of calcium is 7 (McPhalen C A, et al., Advances in Protein Chemistry 1991; 42:77–143), and only 4 coordination sites of $Ca^{2+}$ are occupied by binding to NST401-B, each of these metal ions still has, after this binding, three unoccupied coordination sites. In solution, these sites are occupied by water molecules. However, in the presence of PS, water molecules will be displaced by the negative-charged oxygen atoms of the phosphate and/or the carboxyl moieties of the PS headgroup. In addition, salt bridges may be formed between the —$NH_3^+$ group of the PS headgroup, and the carboxyl moieties of the NST 401-B compound. Alternatively, the nitrogen atom may undergo deprotonation and participate in the coordination of $Ca^{2+}$. As evident from FIG. 4, there is a good three-dimensional fit between these functional units of the $Ca^{2+}$-bound NST401-B compound and the PS headgroup. The myristic acid residue, exemplifying hydrophobic moiety A, further strengthens these interactions by anchoring NST401-B to the membrane.

The present invention also consists in pharmaceutical compositions comprising as active ingredient an NST400 compound or T-NST400 conjugate as defined above. The NST 400 compound or T-NST400 conjugate, as mentioned above, may be either in acid form or pharmaceutically acceptable salts and chelate complexes thereof (such as a complex of NST 400 with $Ca^{2+}$), since physiological conditions in the body, upon administration of the compound (mainly pH, ionic strength and extracellular $Ca^{2++}$ concentrations) allow its activity in either form.

In a preferred embodiment the pharmaceutical composition comprises in addition to the NST400 compound or the T-NST400 conjugate a pharmaceutically acceptable carrier.

The carriers may be selected among any suitable components, e.g. solvents; emulgators; excipients; talc; flavors; colors; etc. The pharmaceutical composition may comprise, if desired, also other pharmaceutically active compounds. The pharmaceutical compositions may be in the form of tablets, capsules, solutions, emulsions, etc.

The pharmaceutical composition according to the present invention may comprise an additional pharmaceutically active compound. Such compound may be a drug useful for the medical condition for which the NST 400 compound or the T-NST 400 conjugate is being administered, by providing either an additional beneficial effect or by reducing potential adverse effects.

The amount of NST400 or T-NST400 conjugate incorporated in the pharmaceutical composition may vary widely. The factors to be considered when determining the precise amount are known to those skilled in the art. Such factors include, inter alia, the pharmaceutical carrier being part of the composition, the route of administration being employed and the frequency of administration.

The pharmaceutical composition may be administered by any of the known methods, inter alia, per os, intravenous, intraperitoneal, intramuscular, subcutaneous, sublingual, intraocular, intranasal or topical administration.

The present invention also consists in a method for binding a negative-charged phospholipid (NCP), preferably phosphatidylserine in biological membranes (PSM). Said method consists of interacting said NCP with either NST400 compound or NST 400 conjugate in the presence of $Ca^{2+}$. The NST400 compound or the NST 400 conjugate may be in solution, for diagnostic and therapeutic purposes; or attached to a solid support, for the purpose of separation and removal of cells and cellular elements with surface exposure of NCP.

The present invention further consists in the use of NST400 or T-NST 400 conjugate in the preparation of a medicament, in particular for the treatment or prevention of the following medical disorders:

1. Thrombotic or prothrombotic states: advantageously for the treatment of disorders which are or are associated with excessive procoagulant activity, such as arterial or venous thrombosis [e.g., myocardial infarction, cerebral stroke, deep vein thrombosis, disseminated intravascular coagulation (DIC)]; sickle cell disease; thalassemia; antiphospholipid antibody syndrome; systemic lupus erythematosus; shed membrane particles, (e.g. during cardiopulmonary bypass); apoptosis; etc.;
2. Urolithiasis;
3. Use T-NST400 conjugate, wherein the NST400 compound is conjugated to an apoptosis inhibitor (e.g., caspase inhibitor or an antioxidant) or inducer (e.g., anticancer drug), for the treatment of disorders of excessive apoptosis (e.g., degenerative disorders such as Alzheimer's or Parkinson's disease) or disorders of decreased apoptosis (e.g., cancer or myeloproliferative disorders), respectively.

The present invention also consists in a method for treatment or prevention of the following medical disorders by administration of an effective amount of NST400 compound or T-NST400 conjugate to a subject in need of such treatment, for example:

1. Thrombotic or prothrombotic states: Advantageously for the treatment of disorders which are or are associated with excessive procoagulant activity, such as arterial or venous thrombosis; myocardial infarction; cerebral stroke; deep vein thrombosis; disseminated intravascular coagulation (DIC); sickle cell disease; thalassemia; antiphospholipid antibody syndrome; systemic lupus erythematosus; shed membrane particles, (e.g. during cardiopulmonary bypass); apoptosis; etc.;
2. Urolithiasis.

The present invention also consists in a method for the treatment or prevention of medical disorders by a T-NST400 conjugate wherein the NST400 compound is conjugated to an apoptosis inhibitor (e.g., caspase inhibitor or an antioxidant) or inducer (e.g., anticancer drug), or by a pharmaceutical composition comprising same. Said medical disorders are diseases of excessive apoptosis (e.g., degenerative disorders such as Alzheimer's or Parkinson's disease) or disorders of decreased apoptosis (e.g., cancer or myeloproliferative disorders), respectively.

The present invention also consists in the use of an T-NST400 conjugate or of a pharmaceutical composition comprising same, wherein the NST400 compound is conjugated to a marker for imaging [e.g. detectors of fluorescence, x-ray, magnetic resonance imaging (MRI), or radioisotope scan]; for the diagnosis of CMLA loss. Said use may be performed either in vitro or in vivo in accordance with the specific requirements. Said uses are especially:

1. Use as a diagnostic agent for the detection and imaging of cell death, particularly of apoptosis, either in vitro or in vivo. The in vitro imaging is preferably performed with fluorescein; the in vivo imaging is preferably performed by a scan with an isotope or by MRI;
2. Use as a diagnostic agent for thrombosis or for prothrombotic states;
3. Use as a diagnostic agent for pathophysiological states associated with apoptosis; e.g. monitoring of response to anticancer treatments, diagnosis of disorders of inappropriate excessive apoptosis, monitoring of response to cytoprotective treatments, monitoring of graft survival following organ transplantion;
4. Use as a diagnostic agent for pathophysiological states associated with urolithiasis.

Said conjugation of the NST400 compound to the marker for imaging, as well as signal detection and analysis will be performed by those of skill, using the respective appropriate imaging equipment.

The present invention also consists in a diagnostic kit comprising a T-NST400 conjugate, wherein the NST400 compound is conjugated to a marker for imaging; or a pharmaceutical comprising same, for the performance of the diagnostic steps, in the presence of $Ca^{2+}$.

The present invention also consists in the use of a T-NST400 conjugate or of a pharmaceutical composition comprising same, as a targeting agent, to target drugs to tissues inflicted by CMLA loss, preferably tissues the cells of which are inflicted by apoptosis, or tissues in which thrombosis takes place. In said T-NST400 conjugate, the NST400 compound will be conjugated to the drug to be targeted, via moiety D of NST400. In the case of targeting apoptosis-inhibitory drugs to tissues inflicted by excessive apoptosis, such drugs may preferably be caspase inhibitors or antioxidants. In the case of targeting drugs to augment apoptosis in tissues, such drugs may preferably be anticancer drugs. In the case of targeting drugs to treat thrombosis, such drugs may preferably be antithrombotic or fibrinolytic agents selected among heparin, low molecular weight heparin, antagonists of glycoprotein IIb/IIIa and tissue plasminogen activator (tPA).

The present invention also consists in a method for targeting drugs to tissues in the body which are inflicted by CMLA loss, which method comprises the administration of T-NST400 conjugate or its pharmaceutical composition, wherein the NST400 compound drug is conjugated to a drug to be targeted to specific tissues. The NST400 moiety directs the conjugate to cells characterized by CMLA loss. At those sites, the targeted drug is expected to accumulate and exert its action, either in the conjugated form, or after cleavage of its linkage to NST400 by tissue specific mechanisms, such as local enzymes. Such enzymes are for example naturally-occurring esterases, in case of linkage of the drug to NST400 by an esteric bond. The tissues are in particular those inflicted by excessive apoptosis, or tissues in which thrombosis takes place. The drugs are in particular drugs that modulate apoptosis, or alternatively, anticoagulant, antithrombotic or thrombolytic drugs.

This method, utilizing T-NST400 conjugates may therefore be useful for treatment of thrombotic and/or prothrombotic disorders associated with arterial or venous thrombosis; myocardial infarction; cerebral stroke; deep vein thrombosis; disseminated intravascular coagulation (DIC); sickle cell disease; thalassemia; antiphospholipid antibody syndrome; systemic lupus erythematosus; shed membrane microparticles; and apoptosis. In these disorders, T-NST400 conjugate may allow the targeting of drugs selected among heparin, low-molecular weight heparin (LMWH), antagonist of glycoprotein IIb/IIIA and tissue plasminogen activator (tPA), thus enabling potentiation of their local effect, while avoiding untoward systemic anticoagulation.

Alternatively, this method utilizing T-NST400 conjugate may allow targeting of inhibitors of apoptosis, such as caspase inhibitors to tissues inflicted by excessive apoptosis, enabling modulation of the fate of these tissues, while avoiding systemic perturbation of apoptosis control. Therefore, this method may be useful for the treatment of disorders such as degenerative diseases, myelodysplastic disorders, AIDS, ischemic or toxic insults.

Such method, wherein T-NST400 conjugate comprises an anticancer drug may also be useful for enhancing the efficacy of anticancer protocols. For this purpose, a first wave of apoptosis will be induced in a tumor by standard radiotherapy or chemotherapy. As a second stage, administration of T-NST400 conjugate comprising the anticancer drug may be performed. Said T-NST400 conjugate will be targeted to the apoptotic cells within the tumor, thus augmenting the local levels of the anticancer treatment.

The present invention also consists in the use of NST400 compounds, or T-NST400 conjugates, or of pharmaceutical compositions comprising same, in the presence of $Ca^{2+}$, for basic research, in fields of research in which CMLA loss takes place, both in vitro and in vivo, inter alia, of cell cultures, preferably in basic research of apoptosis and blood coagulation.

The present invention consists also in NST400 compound or T-NST400 conjugate being attached to a solid support, and being part of an affinity filter. Due to the binding of NCP to the NST400 compounds or T-NST400 conjugates attached to the solid support, said filter will be effective in capturing and thereby removing particles having surface exposure of NCP, such as apoptotic cells, apoptotic bodies, activated platelets, platelet-derived microparticles, cell debris and platelet-fibrin clots. Said particles being present in body fluids, such as blood or blood-derived products. The present invention also consists in the use of said affinity filter.

The present invention also consists in a method of capturing and thereby removing particles characterized by surface exposure of NCP. Said particles being present in body fluids, such as blood or blood-derived products. The method comprises the step of directing the body fluid through an affinity filter. Said filter including a body, containing a solid support and a NST400 compound or T-NST400 conjugate linked to the solid support. Due to the binding of NCP to the NST400 compound or the T-NST400 cojugate attached to the solid support, said filter will be effective in capturing and thereby removing particles having surface exposure of NCP, such as apoptotic cells, apoptotic bodies, activated platelets, platelet-derived microparticies, cell debris and platelet-fibrin clots. This capturing and removal of these particles will allow improvement of the quality of the body fluid and reduce its thrombogenity. Preferably, said filter may be used to improve blood quality and remove microemboli generated during extracorporeal circulation (e.g., during cardiopulmonary bypass procedures). Such microemboli, largely composed of NCP-exposing elements are currently viewed as a major cause of frequent neurological morbidity complicating these procedure (Pugsley et al., Stroke 1994; 25:1393–1399).

The present invention will now be illustrated with reference to the examples and to the accompanying drawings without being limited by same.

In said drawings:

The patent or application file contains at least one drawing executed in color. Copies of this patent with color drawing(s) will be provided by the Patent and Trademark Office upon request and payment of necessary fee.

Figure 2:
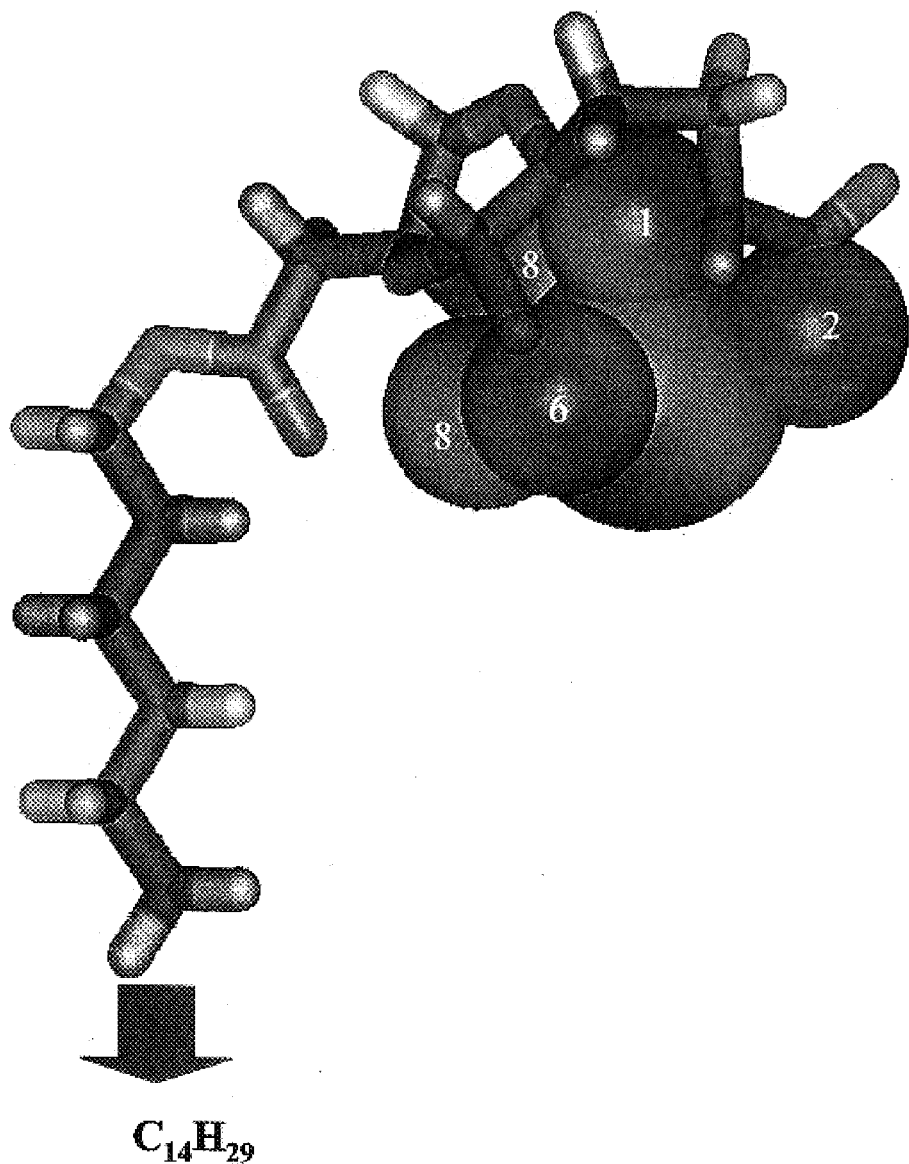

FIG. 1: Shows the structure of NST401-B (in its anionic form);

FIG. 2: Shows molecular simulation of chelation of one $Ca^{2+}$ ion by NST401-B.

Figure 3:
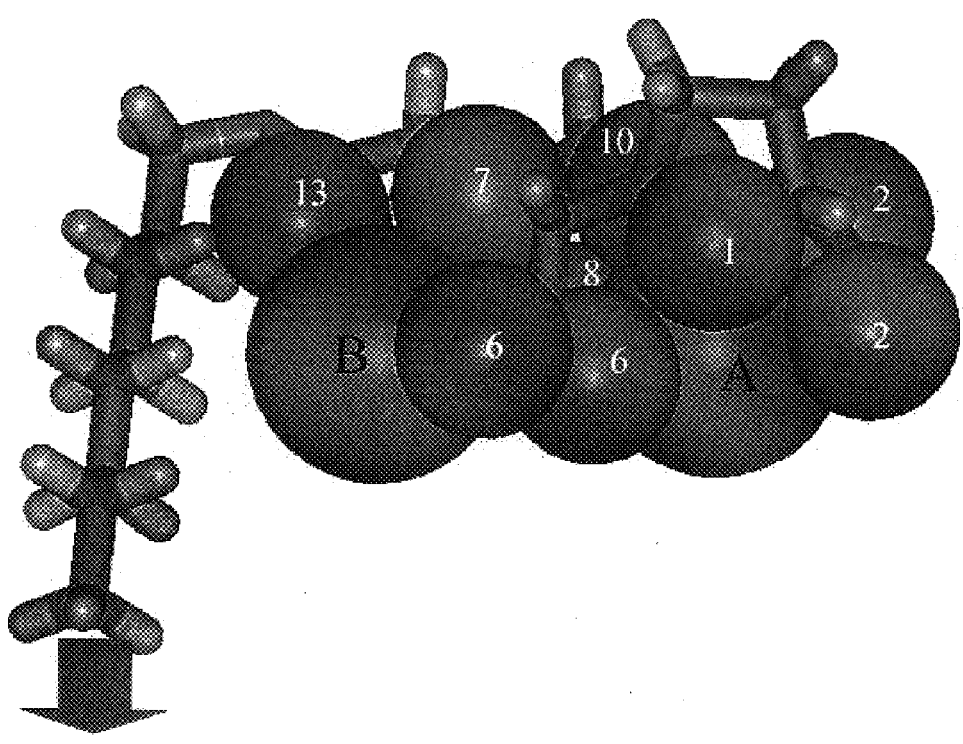

FIG. 3: Shows molecular simulation of chelation of two $Ca^{2+}$ ions by NST401-B.

Figure 4:
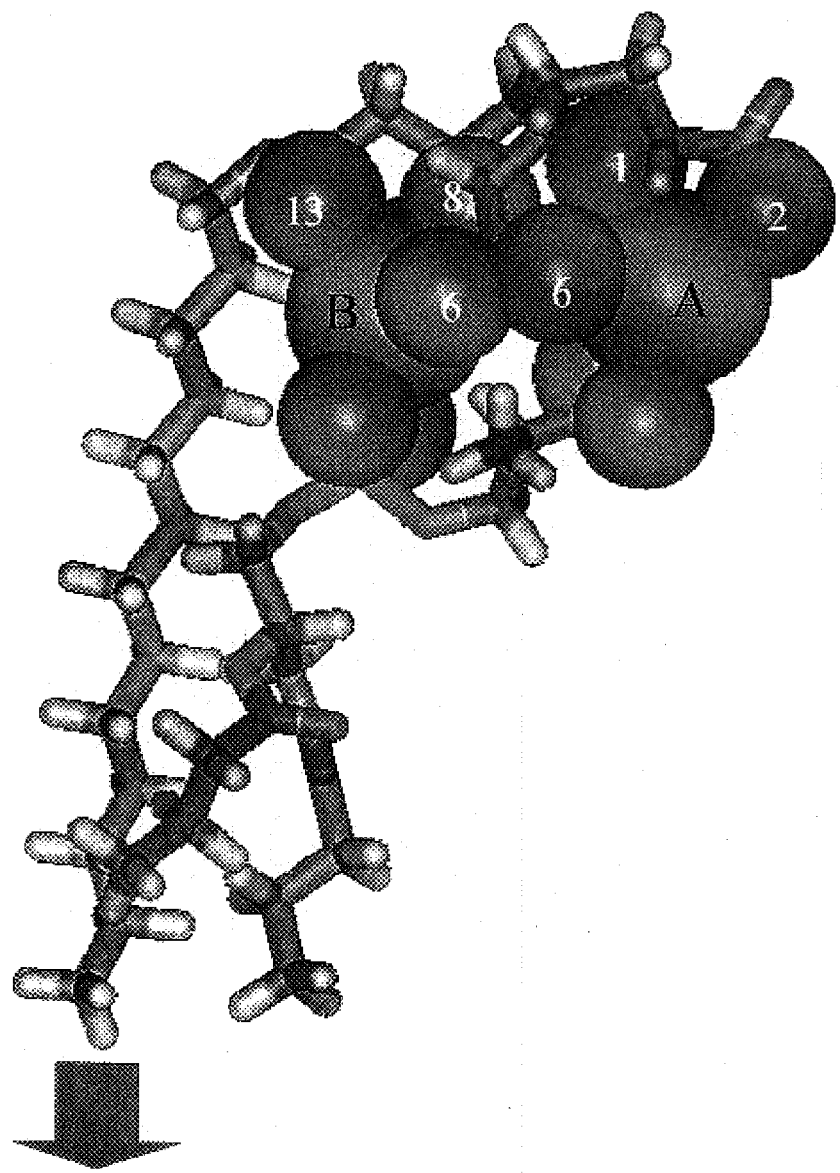

FIG. 4: Shows molecular simulation of NST401-B, in complex with two $Ca^{2+}$ ions and phsphatidylserine (PS).

THE DETAILED EXPLANATION OF THE FIGURES IS GIVEN HEREUNDER

FIG. 1: Structure of NST401-B.

Stick presentation of the NST401-B compound. (In the coloured figures Carbon atoms are marked green, hydrogen atoms white, oxygen atoms red). The coordinating oxygen atoms (CA) that constitute the $Ca^{2+}$ binding sites (CBS) are numbered. Only 4 of the 14 carbon atoms of the acyl chain are presented, the others being marked by the arrow.

FIG. 2: NST401-B, Molecular Simulation of Binding of One $Ca^{2+}$ Ion.

NST401-B is presented as in FIG. 1; the $Ca^{2+}$ atom being marked as a big ball (in the coloured figures, pink), and the coordinating oxygen atoms (CA) of the metal ion being marked as small balls. The Figure demonstrates the structural capability of NST401-B to provide appropriate three-dimensional arrangement of coordinating oxygen atoms (CA), to allow partial coordination one $Ca^{2+}$ ion. The ion is coordinated by ether oxygen 1, by oxygen atoms of carboxyl groups 2 and 6, and to a lesser extent by carboxyl 8. Yet the metal ion remains partially exposed, having several unoccupied coordination sites.

FIG. 3: NST401-B, Molecular Simulation of Binding of Two $Ca^{2+}$ Ions.

NST401-B and $Ca^{2+}$ ions are presented as in FIGS. 1 and 2, respectively. The Figure demonstrates the structural capability of NST401-D to provide appropriate three-dimensional arrangement of coordinating atoms (CA) to allow partial coordination of two $Ca^{2+}$ ions: each metal ion is coordinated by four CA's: $Ca^{2+}$ ion A is coordinated by ether oxygens 1 and 10 and carboxyl groups 2 and 6; $Ca^{2+}$ ion B is coordinated by carbonyl 13, carboxyl groups 6 and 8, and by ether oxygen 7. Carboxyl 6 is therefore positioned to coordinate both metal ions. Following binding to NST401-B, each $Ca^{2+}$ ion is however still partially exposed, maintaining unoccupied coordination sites.

FIG. 4: Molecular Simulation of NST401-B, in Complex with Two $Ca^{2+}$ Ions and Phsphatidylserine (PS).

NST401-B and $Ca^{2+}$ ions are presented as in FIGS. 1, 2 and 3. Unoccupied coordination sites of metal ions A and B, demonstrated in FIG. 3, are now occupied by the carboxyl and phosphate oxygen atoms, respectively. The amine group of PS is in appropriate orientation to form a salt bridge with carboxyl 6.

EXAMPLE 1

NST401-B: Geometry of $Ca^{2+}$ Coordination; Molecular Simulation

The objective of this experiment was to determine, using state-of-the-art molecular modeling tools, the level of conformity of the three-dimensional orientation of the calcium coordinating atoms (CA's) of the NST401-B to the pentagonal bipyramidal arrangement, characteristic of $Ca^{2+}$ coordination.

$Ca^{2+}$ preferably accommodates seven CA's in its primary coordination sphere (heptacoordinate $Ca^{2+}$). The mean $Ca^{2+}$—CA distance is 2.4 Å, and the CA's are arranged regularly around the $Ca^{2+}$ ion, forming a pentagonal bipyramid, with five CA's in an equatorial plane (McPhalen C A, et al., Advances in Protein Chemistry 1991: 42:77–144). In numerous x-ray crystal structures of small molecule calcium chelators as well as in calcium-binding proteins, these rules has been shown to be a prerequisite for high-affinity $Ca^{2+}$ binding. Current Example shows that NST401-B provides the proper three-dimensional orientation of CA's, required for effective binding of $Ca^{2+}$.

Methods: Molecular simulations, i.e., molecular modeling, molecular dynamics simulation and energy minimization were performed following the guidelines by Leach A L (Leach A L, Molecular Modeling; Principles and Applications, Longman Publishers Ltd. Singapore; 1997). The Insight-II-Discover 95 software package was used [Molecular Simulations Inc., CA, U.S.A. (MSI)], and computations were performed on a Silicon Graphics Octane workstation (Silicon Graphics, Inc., CA, U.S.A.). The force-field used was the cvff (consistent-valence force field) by MSI, a widely-used, experimentally-validated force-field (Hagler A T, et al. J. Am. Chem. Soc. 1977; 96:5327–5335; Dauber-Osguthorpe P., et al., Proteins: Structure, Function and Genetics 1988; 4:31–47; Dinur U., & Hagler A T. in: Lipkwowitz K B, & Boyd, D B, Eds.; Reviews of Computational Chemistry; VCH, New York 1991, vol. 2). The dielectric constant to be used for the simulations (2r) was chosen following a calibration experiment performed with the potent, well known $Ca^{2+}$ chelator DOTA (tetraazacyclododecane N,N'N",N'"teteraacetic acid). In said experiment, the $Ca^{2+}$—O distances obtained by the computerized simulation system using various dielectric parameters, were compared to the values obtained in X-ray defraction experiments of $Ca^{2+}$.DOTA complex (Aderson O P, et al., Acta Crystall. 1996; 52:792–795). In the above dielectric parameter, the mean calculated distance (2.46±0.03 Å), was in an excellent agreement with the mean experimentally-measured distance of 2.45±0.03 Å.

The starting structural conformations of: (1): NST401-B; (2): NST401-B in complex with one $Ca^{2+}$ ion; and (3): NST401-B in complex with two $Ca^{2+}$ ions were built using the Insight-II builder module. Structures were then optimized by energy minimization, followed by molecular dynamics simulation. Energy minimization was performed using the Steepest Descent algorithm; 75 iterations or until the maximum derivative was less than 0.05 kcal/Å; followed by the Conjugate Gradient algorithm; with the endpoint of a maximum derivative being less than 0.05 kcal/Å (Leach A R., Molecular Modeling. Longman, Harlow, England; 1996: Chap. 4; Jorgensen H. et al., Protein Engineering 1993; 6:19–23; Meller J, et al., Biophys. J. 1998; 74:789–802). The minimized structures were then subjected to a conformation search, using molecular dynamics simulation and energy minimization, in order to find the lowest-energy structural conformation (Fossheim R, et al., Acta Chem. Scand. 1990; 44:698–706; Liu Z P & Gierasch L M, Biopolymers 1992; 32:1727–1739). Simulation time was 110 ps, in 315° K, after 10 ps of equilibration. Conformation analysis and energy minimization were performed every 1000 steps of 1 fs each. The lowest energy structural conformation of each structure was then taken for evaluation of its fit to the ideal pentagonal bipyramid of $Ca^{2+}$ coordination.

The ideal pentagonal bipyramid of $Ca^{2+}$ coordination geometry, with a 2.4 Å distance from its center to each of its vertices was also built, and was then superimposed on the above molecular structure. Fit of the geometry of calcium coordination by NST401-B to the ideal polygon was determining by calculating the root mean square deviation (RMSD), using the formula RMSD=$(\Sigma d_i^2/N_{atoms})^{1/2}$, wherein $N_{atoms}$ is the number of pairs of superimposed points, and $d_i$ is the distance between coordinates of the points i in the two structures, upon superimposition (Leach A R, Molecular Modeling. Longman, Harlow, Essex, England; 1996; Chap. 8).

Results: As shown in FIG. 2, binding of one $Ca^{2+}$ ion to NST401-B is provided by several coordinating atoms: ether oxygen 1, and oxygen atoms of carboxyl groups 2 and 6, and to a lesser extent carboxyl 8. Evaluation of fitting of the three-dimensional orientation of these CA to the ideal pentagonal bipyramid yielded an RMSD value of 0.37 Å. The average distance of these CA from the $Ca^{2+}$ ion was 2.42 Å.

As shown in FIG. 3, binding of two $Ca^{2+}$ ions to NST401-B is as follows: $Ca^{2+}$ ion A is coordinated by ether oxygens 1 and 10, oxygen atoms of carboxyl groups 2, and 6; $Ca^{2+}$ ion B is coordinated by carbonyl 13, oxygen atoms of carboxyl groups 6 and 8, and by ether oxygen 7. Carboxyl 6 is therefore positioned to coordinate both metal ions. The fit of the three-dimensional orientation of these CA's to the ideal polygon was characterized by RMSD values of 0.39 Å and 0.41 Å for $Ca^{2+}$ atoms A and B, respectively. The average distances of CA's from the coordinated metal ions were 2.52 Å and 2.43 Å for $Ca^{2+}$ ions A and B, respectively.

These calculated RMSD and CA—$Ca^{2+}$ distances of binding of $Ca^{2+}$ to NST401-B are in a very good agreement with the structural features of $Ca^{2+}$ binding sites in numerous $Ca^{2+}$-binding molecules. For example, McPhalen et al. performed structural analysis of calcium binding sites of 20 calcium-binding proteins, with 182 CA's within these proteins, based on x-ray crystallographic data. Average RMSD of CA's from the ideal pentagonal bipyramid was found to be 0.41±0.05 Å, while average CA—$Ca^{2+}$ distance was 2.4±0.2 Å (mean±SD); (McPhalen C A, et al. Adv. Protein Chem., 1991: 42:77–144).

EXAMPLE 2

NST401-B: Molecular Simulation: Expected Energetic Advantage from Binding to $Ca^{2+}$ Ions and Binding to Phsophatidylserine (PS)

The objective of this example is to provide evidence for the energy benefit, expected from binding of $Ca^{2+}$ ions to NST401-B compound, as well as the expected benefit of binding of $Ca_{(1-2)}^{2+}$.NST401-B complex to PS.

Methods: Molecular simulation was performed as described in Example 1. The minimized, lowest-energy conformation of each compound/complex was used for the analysis. The total energy calculated in the model (E) was the summation of: (1). Non-bond energies components: non-bond repulsion energies, non-bond dispersion energies and Coloumb energies; and (2): Bond energy components: bond energies, angle energies, dihedral energies and out of plane energies (Leach A R, Molecular Modeling. Longman, Harlow, England; 1994; Chapt. 4).

The energy of each interaction ($\Delta E_{interaction}$) was calculated as follows: (1). Calculation of the sum of the energies of the reactants at their minimum models (Er). (2). Calculation of the minimum energy of the reaction product model (Ep). (2) Calculation of the difference between the energy of the products and the reactants ($\Delta E_{interaction}$=Ep−Er). The $\Delta E_{interaction}$ reflects an essential component of complex stability. However, it does not reflect the entropy component of the free energy of binding.

Results: The $\Delta E_{interaction}$ of the various complexes are presented in Table 1:

| Interarction | $\Delta E_{interaction}$(Kcal/mole) |
| --- | --- |
| NST401-B + 1Ca$^{2+}$ | −302.43 |
| NST401-B + 2Ca$^{2+}$ | −448.08 |
| NST401-B + PS + 1Ca$^{2+}$ | −45.54 |
| NST401-B + PS + 2Ca$^{2+}$ | −115.33 |

Conclusions: Binding of one or both Ca$^{2+}$ ions to NST401-B is predicted to be associated with a significant energy loss, and thus is favorable. Formation of complexes of phosphatidylserine with $Ca_{(1-2)}^{2+}$.NST401-B is also predicted to be a remarkably energetically-favorable process.

EXAMPLE 3

Synthesis of NST401-D

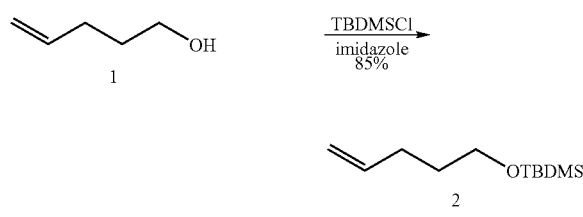

To a stirred 75 mL DMF solution of alcohol 1 (5.4 g, 63 mmol) and imidazole (4.5 g, 66 mmol) at 0° C. was added TBDMSCI (10 g, 66 mmol). The reaction was stirred 15 min at 0° C. and 1 h at RT at which time the alcohol 1 could not be detected by TLC analysis. The reaction was diluted with 400 mL of hexanes and washed successively with water (4×100 mL) and saturated brine (50 mL). The organic layer was dried (MgSO$_4$), filtered through a pad of silica gel and concentrated. The residual solvents removed in vacuo (<1 mmHg) overnight to provide 10.7 g (85%) of 2 as a thick oil.

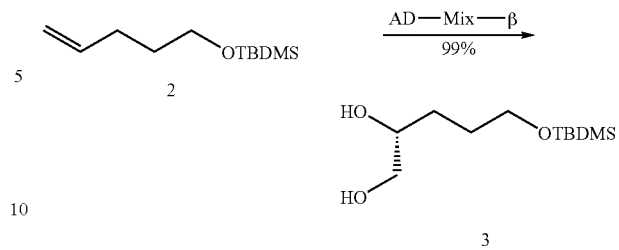

AD-Mix-β™ (50 g, 1.4 g/mmol) was added to 350 mL of 1:1 tert-butyl alcohol:water and stirred for 1 h at RT before being cooled to 0° C. The silyl-ether 2 (7.1 g, 35 mmol) was then added in one portion to the orange slurry. After 4 h at 0° C., no starting material could be detected by TLC analysis and the reaction was quenched with 50 g of sodium sulfite and stirred at RT for 30 min. The aqueous layer was extracted with ethyl acetate (3×200 mL). The combined organic layers were diluted with 100 mL of hexanes, dried (MgSO$_4$) and filtered through a pad of silica gel. The pad of silica gel was washed with an additional 400 mL of 3:1 ethyl acetate:hexanes. The combined organic solutions were concentrated and residual solvents removed in vacuo (<1 mmHg) overnight to provide 8.1 g (99%) of 3 as a thick syrup.

Reference: Sharpless, K. B.; Amberg, W.; Bennani, Y. L.; Crispino, G. A.; Hartung, J.; Jeong, K. -S.; Kwong, H. -L.; Morikawa, K.; Wang, Z. -M.; Xu, D.; Zhang, X. -L. *J. Org. Chem.* 1992, 57, 2768.

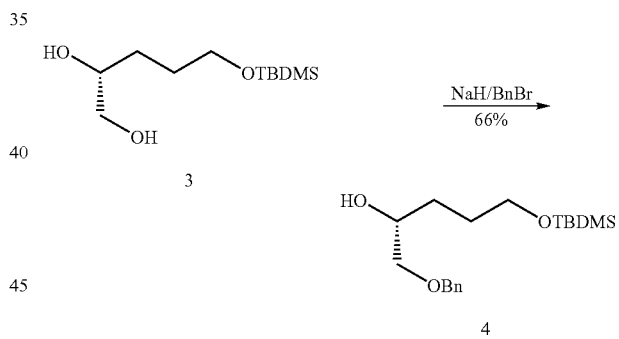

To a rapidly stirred 80 mL THF slurry of NaH (1.7 g of a 60% dispersion in mineral oil, 42 mmol) at 0° C. was added a 30 mL THF solution of diol 3 (7.8 g, 33 mmol) dropwise over 20 minutes. The reaction was stirred for 1 h at 0° C. and cooled to −78° C. before adding neat benzyl bromide (3.9 mL, 33 mmol) via syringe. The reaction was stirred for 30 min before being warmed to 0° C. for 2 h and RT overnight. TLC analysis indicated that the reaction was nearly complete. An additional 0.4 g of NaH dispersion was added and the reaction stirred at RT for 4 hours. The reaction was quenched with 10 mL of saturated NH$_4$Cl then diluted with 200 mL of Et$_2$O and 100 mL of water. The layers were separated and the aqueous layer was extracted with Et$_2$O (3×100 mL). The combined organic layers were washed with saturated brine (50 mL), dried (MgSO$_4$), filtered and concentrated. The crude product was purified by flash chromatography (5:1 hexanes:ethyl acetate, R$_f$ 0.45) to provide 7.1 g (66%) of 4 as a thick oil.

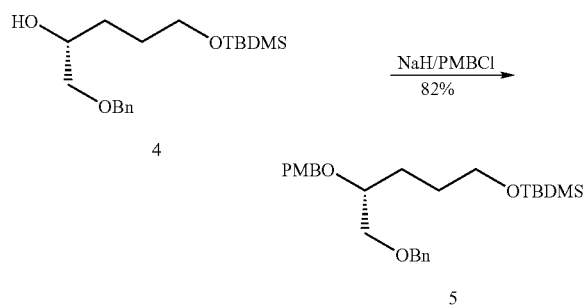

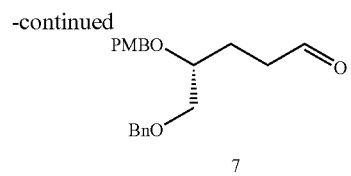

A slurry of NaH (1.2 g of a 60% dispersion in mineral oil, 30 mmol) in 30 mL of dry DMF was treated with a 15 mL DMF solution of 4 (6.9 g, 21 mmol) dropwise over 30 minutes. The reaction was stirred for 2 h at RT before adding neat p-methoxybenzyl chloride (3.4 mL, 25 mmol) via syringe. The reaction was stirred at RT overnight at which time no starting alcohol 4 could be detected by TLC analysis. The reaction was quenched by pouring into 200 mL of ice water and the resulting mixture was extracted with 5:1 hexanes: Et$_2$O (4×100 mL). The combined organic layers were dried (MgSO$_4$), filtered and concentrated. The crude product was purified by flash chromatography (8:1 hexanes: ethyl acetate, R$_f$ 0.38) to provide 7.6 g (82%) of 5 as a thick oil.

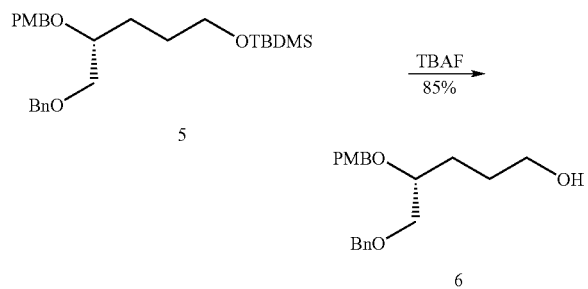

The differentially protected triol 5 (7.0 g, 16 mmol) was dissolved in 30 mL of bulk THF and treated with tetrabutylammonium fluoride (32 mL of 1.0 M THF solution, 32 mmol). The reaction was stirred for 1 h at RT at which time only a trace of 5 could be detected by TLC analysis. The solvent was removed by rotary evaporation and the crude oil was dissolved in 300 mL of CH$_2$Cl$_2$. The solution was washed with 100 mL of water and the aqueous solution was back-extracted with 100 mL of CH$_2$Cl$_2$. The combined organic layers were dried (MgSO$_4$), filtered and concentrated. The crude product was purified by flash chromatography (1:1 hexanes:ethyl acetate, R$_f$ 0.40) to provide 4.4 g (85%) of 6 as a thick oil.

Reference: Prabhakaran, P. C.; Gould, S. J.; Orr, G. R.; Coward, J. K. *J. Am. Chem. Soc.* 1988, 110, 5779.

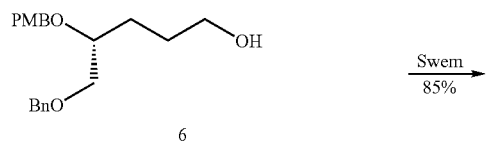

The alcohol 6 (1.3 g, 3.9 mmol) was dissolved in 10 mL of CH$_2$Cl$_2$, cooled to 0° C. and triethylamine (2.7 mL, 19 mmol) was added. To the reaction mixture was added pyridine-sulfur trioxide (0.94 g, 5.9 mmol) dissolved in 6 mL of dry DMSO via syringe. The reaction was stirred at 0° C. for 3 h at which time alcohol 6 could not be detected by TLC analysis. The reaction was quenched with 30 mL of saturated NaHCO$_3$ and 10 mL of water. The layers were separated and the aqueous layer was extracted with 3:1 Et$_2$O:hexanes (3×80 mL). The combined organic layers were washed with 1 M NaH$_2$PO$_4$ (50 mL) and saturated brine (50 mL) then dried (MgSO$_4$), filtered and concentrated. The crude product was purified by flash chromatography (3:2 hexanes:ethyl acetate, R$_f$ 0.32) to provide 1.1 g (85%) of 7 as an oil.

Reference: Wipf, P., Fritch, P. C. *J. Org. Chem.* 1994, 59, 4875.

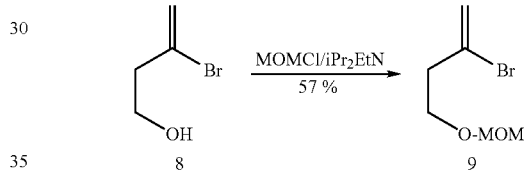

The alcohol 8 (7.6 g, 50 mmol) was treated dissolved in 50 mL of CH$_2$Cl$_2$, cooled to 0° C. and treated with diisopropylethyl amine (26 mL, 150 mmol) and methoxymethyl chloride (4.5 mL, 50 mmol) sequentially. The reaction was stirred overnight at RT at which time alcohol 8 could be detected by TLC analysis. The reaction was quenched with 2:1 saturated NaHCO$_3$:water (60 mL) and the solvent removed by rotary evaporation. The resulting crude material was extracted with Et$_2$O (3×100 mL). The combined organic layers were dried (MgSO$_4$), filtered through a pad of silica gel and concentrated. Removal of residual solvent in vacuo (<1 mmHg) provided 5.5 g (57%) of 9 as an oil.

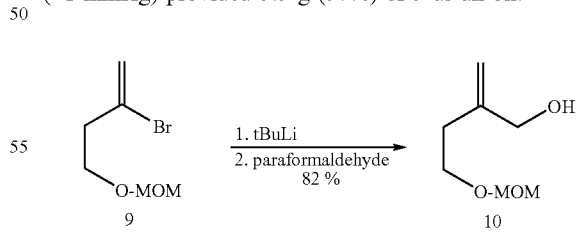

The acetal 9 (5.5 g, 27 mmol) was dissolved in 75 mL of dry Et$_2$O, cooled to −78° C. and treated with tert-butyllithium in pentane (41 mL of 1.7 M solution, 70 mmol) dropwise over 30 min. The reaction was stirred at −78° C. for 10 min followed by addition of an Et$_2$O (50 mL) slurry of paraformaldehyde (0.99 g, 33 mmol). The reaction was allowed to warm to RT overnight at which time acetal 9 could not be detected by GC analysis. The reaction was quenched with 2:1 water:saturated NaHCO$_3$ and extracted with ethyl acetate (5×75 mL). The combined organic layers were dried (MgSO$_4$), filtered through a pad of silica gel and concentrated. The crude product was purified by flash chromatography (1:1 hexanes:ethyl acetate, R$_f$ 0.40) to provide 3.2 g (82%) of 10 as an oil.

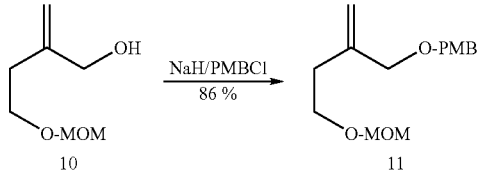

A slurry of NaH (1.3 g of a 60% dispersion in mineral oil, 33 mmol) in 20 mL of dry DMF was treated with a 10 mL DMF solution of 10 (3.1 g, 21 mmol) dropwise over 30 minutes. The reaction was stirred for 30 min at RT before adding neat p-methoxybenzyl chloride (3.6 mL, 27 mmol) via syringe at which time an exotherm was observed and the reaction was cooled to 0° C. for 10 min. The reaction was allowed to warm to RT and was stirred overnight at which time GC analysis indicated that the reaction was essentially complete (approximately 3% of 10 was detected). The reaction was quenched by pouring into 250 mL of ice water and the resulting mixture was extracted with 5:1 Et$_2$O: hexanes (5×100 mL). The combined organic layers were dried (Na$_2$SO$_4$), filtered and concentrated. The crude product was purified by flash chromatography (3:1 hexanes:ethyl acetate, R$_f$ 0.38) to provide 4.8 g (86%) of 5 as an oil.

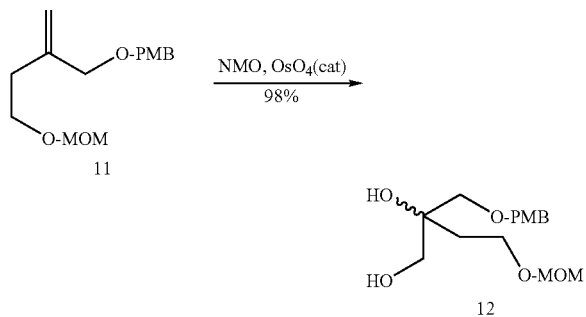

A mixture of 25 mL of tert-butyl alcohol, 25 mL of acetone and 10 mL of water containing OsO$_4$ (0.13 g, 0.5 mmol) was cooled to 0° C. To this solution was added solid NMO monohydrate (1.6 g, 12 mmol) followed by the alkene 11 (2.80 g, 10.5 mmol) in 50 mL of acetone. The reaction was allowed to warm to RT overnight at which time alkene 11 could not be detected by TLC analysis. The reaction was quenched with 15 g of Na$_2$SO$_3$, filtered and concentrated to a 100 mL volume. The aqueous solution was saturated with NaCl and extracted with ethyl acetate (3×100 mL). The combined organic layers were dried (MgSO$_4$), filtered and concentrated. The crude product was purified by flash chromatography (neat ethyl acetate, R$_f$ 0.50) to provide 3.08 g (98%) of 12 as a syrup.

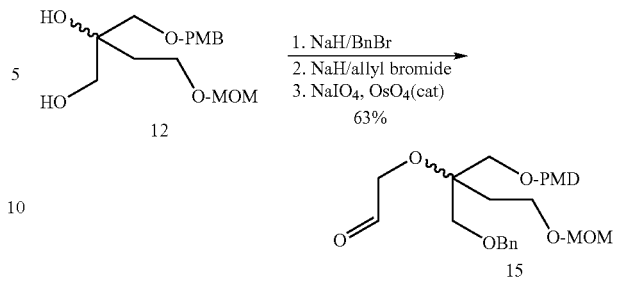

A slurry of NaH (0.88 g of a 60% dispersion in mineral oil, 22 mmol) in 30 mL of dry THF was treated with a 30 mL THF solution of 12 (4.40 g, 14.6 mmol) and stirred at RT for 45 min. Neat benzyl bromide (1.9 mL, 16 mmol) was then added via syringe and the reaction was stirred at RT overnight. The reaction was quenched with 30 mL of water and concentrated. The aqueous layer was extracted with Et$_2$O (3×100 mL), dried (MgSO$_4$), filtered and concentrated to provide crude benzylated material 13. The crude product thus obtained was added as a 30 mL solution in dry DMF to a 30 mL DMF slurry of NaH (0.90 g of a 60% dispersion in mineral oil, 23 mmol) at RT. The reaction was stirred 1 h and neat allyl bromide (2.0 mL, 23 mmol) was added via syringe and the reaction was stirred overnight at RT. The reaction was quenched with water to a 300 mL volume. The solution was extracted with 1:1 hexanes:Et$_2$O (4×100 mL) and the combined organic layers were washed with water (100 mL) and saturated brine (100 mL). The resulting organic solution was dried (MgSO$_4$), filtered through a pad of silica gel and concentrated to provide crude allylated material 14. The crude product thus obtained was dissolved in 200 mL of 1:1 THF:acetone, treated with OsO$_4$ (0.1 g, 0.4 mmol) and cooled to 0° C. before being treated with NaIO$_4$ (16.5 g, 77 mmol). The slurry was stirred at 0° C. for 10 min before removing the cold bath. The reaction was stirred overnight at RT at which time both product and starting material were observed by TLC analysis. An additional 0.1 g of OsO$_4$ was added and the reaction stirred at RT an additional 24 h at which time no starting alkene could be detected by TLC analysis. The solvent was removed by rotary evaporation and the resulting aqueous material was extracted with Et$_2$O (4×100 mL). The combined organic layers were dried (MgSO$_4$), filtered through a pad of celite and concentrated. The crude product was purified by flash chromatography (1:1 to 2:3 hexanes:ethyl acetate, R$_f$ 0.31 with 1:1 hexanes: ethyl acetate) to provide 4.1 g (63% based on 12) of 15 as an oil.

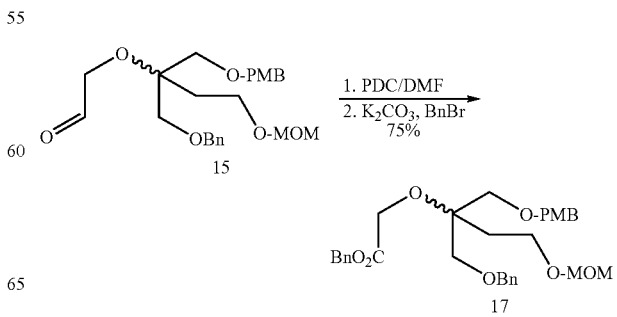

To a 20 mL DMF solution of aldehyde 15 (1.9 g, 4.4 mmol) at RT was added PDC (5.0 g, 13 mmol). After 5.5 h at RT, aldehyde 15 could be detected by TLC analysis. The reaction was diluted with water (150 mL) and extracted with Et$_2$O (6×100 mL). The combined organic layers were dried (MgSO$_4$), filtered through a pad of celite and concentrated to give crude acid 16. The crude product thus obtained was dissolved in acetone (75 mL) and treated with K$_2$CO$_3$ (1.4 g, 10 mmol) followed by benzyl bromide (1.2 mL, 10 mmol). The reaction was heated to 50° C. for 24 h then allowed to cool to RT before removing volatile components by rotary evaporation. The crude product was dissolved in 100 mL of water and extracted with ethyl acetate (3×100 mL). The combined organic layers were dried (MgSO$_4$), filtered and concentrated. The crude product was purified by flash chromatography (2:1 hexanes:ethyl acetate, R$_f$ 0.31 with 1:1 hexanes:ethyl acetate) to provide 1.8 g (75% based on 15) of 17 as an oil.

References: Corey, E. J.; Schmidt, G. *Tetrahedron Lett.* 1979, 20, 399, and Moore, G. G.; Foglia, T. A.; McGahan, T. J. *J. Org. Chem.* 1979, 44, 2425.

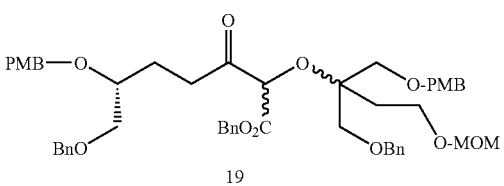

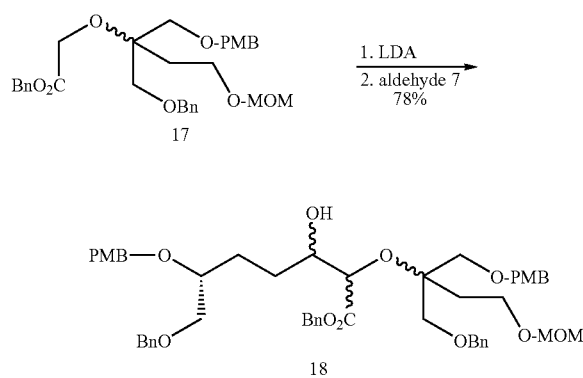

To a pre-formed LDA solution (prepared from 1.9 mL, 4.4 mmol of 2.35 M nBuLi in hexanes and 0.62 mL, 4.4 mmol of diisopropyl amine in 8 mL of THF) at −78° C. was added the benzyl ester 17 (2.0 g, 3.7 mmol) in 8 mL of THF via cannula over 10 min. The yellow-orange solution was stirred an additional 40 min before adding the aldehyde 7 (1.4 g, 4.3 mmol) in 8 mL of THF via cannula over a few minutes and removing the cold bath. No benzyl ester 17 could be detected by TLC analysis of the reaction mixture after 30 min. The reaction was quenched by pouring into 80 mL of saturated NaHCO$_3$ and extracting with Et$_2$O (4×50 mL). The combined organic layers were dried (MgSO$_4$), filtered and concentrated. The crude product was purified by flash chromatography (5:4 hexanes:ethyl acetate, R$_f$ 0.36 and 0.41) to provide 2.5 g (78% based on 17) of the oil 18 as a mixture of diastereomers.

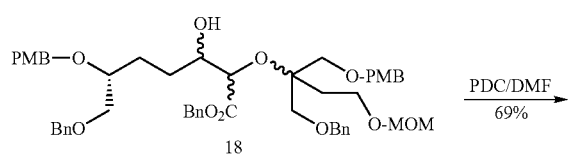

The diastereomeric hydroxyesters 18 (2.1 g, 2.4 mmol) were dissolved in 15 mL of DMF, cooled to 0° C. and treated with PDC (4.5 g, 12 mmol). After 1 h at 0° C., the reaction was allowed to warm to RT and stirred overnight. After 18 h at RT a trace of 18 could be detected by TLC analysis and the reaction was quenched with water (150 mL). The mixture was extracted with Et$_2$O (5×100 mL) and the combined extracts were dried (MgSO$_4$), filtered and concentrated to an approximately 300 mL volume at which point water was observed in the flask. The crude material was dried again (MgSO$_4$), filtered and concentrated to give 2.3 g of a thick, light yellow oil. The crude product was purified by flash chromatography (2:1 to 1:1 hexanes:ethyl acetate, R$_f$ 0.45 with 2:1 hexanes:ethyl acetate) to provide 0.5 g of hydroxyester 18 and 1.1 g (69% based on recovered 18) of the oil 19 as a mixture of diastereomers.

Reference: Corey, E. J.; Schmidt, G. *Tetrahedron Lett.* 1979, 20, 399.

The ketoester 19 (0.50 g, 0.58 mmol) was dissolved in 15 mL of CH$_2$Cl$_2$ and 0.75 mL of water. The solution was then treated with DDQ (0.30 g, 1.3 mmol) at RT to provide a deep green solution. After 1 h at RT, the reaction had turned brown and a solid precipitate was observed. No ketoester 19 (or mono-deprotected intermediates) could be detected by TLC analysis. The reaction was diluted with 150 mL of CH$_2$Cl$_2$, dried (MgSO$_4$), filtered through a pad of celite and concentrated to provide 0.6 g of a red-brown viscous oil. The crude product was purified by flash chromatography (1:3 hexanes:ethyl acetate, R$_f$ 0.3 to 0.5, diffuse spot) to provide 0.27 g (75%) of 20 as a thick oil.

Reference: Oikawa, Y.; Yoshioka, T.; Yonemitsu, O. *Tetrahedron Lett.* 1982, 23, 885.

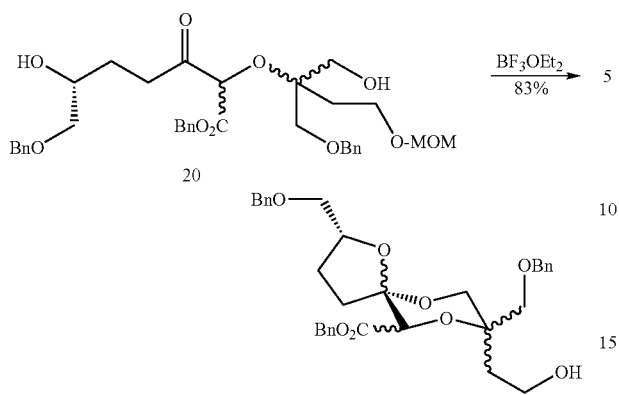

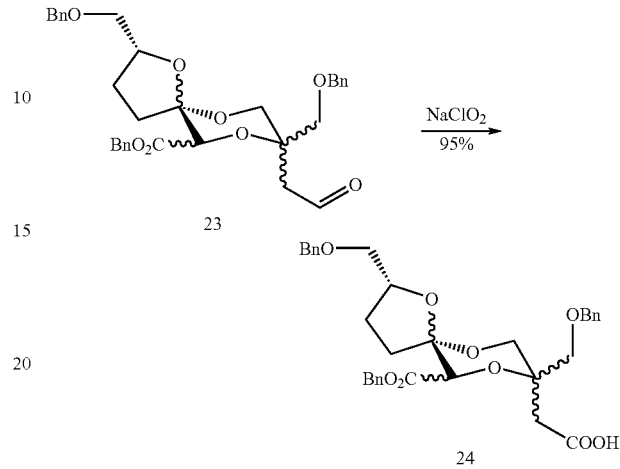

The ketoester 20 (0.95 g, 1.5 mmol) was dissolved in 15 mL of dry CH$_2$Cl$_2$, cooled to −20° C. and treated sequentially with ethyl mercaptan (0.75 mL, 5% v/v) and BF$_3$OEt$_2$ (0.25 mL, 1.9 mmol). The reaction was allowed to warm to RT slowly. After 3 h at RT, the spiroketal 21 (with the MOM group still intact) could still be detected by TLC analysis so an additional 0.10 mL (0.8 mmol) of BF$_3$OEt$_2$ was added. After 1 additional hour, no spiroketal 21 was observed and the reaction was quenched. The reaction was diluted with 50 mL of Et$_2$O and 20 mL of saturated NaHCO$_3$ was added. The aqueous layer was extracted with Et$_2$O and the combined organic layers were dried (MgSO$_4$), filtered and concentrated. The crude product was purified by flash chromatography (2:1 to 1:1 hexanes:ethyl acetate) to provide 0.70 g (83%) of a mixture of four diastereomers of 22.

Reference: Nambiar, K. P.; Mitra, A. *Tetrahedron Lett.* 1994, 35, 3033.

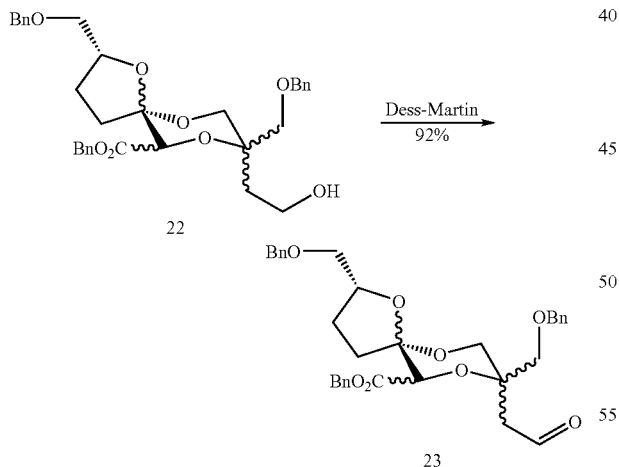

To the spiroketal 22 (180 mg, 0.320 mmol) in 6 mL of CH$_2$Cl$_2$ was added Dess-Martin periodinane (176 mg, 0.415 mmol) and the resulting mixture stirred for 45 min. The reaction was diluted to 60 mL with Et$_2$O and poured into 15 mL of saturated NaHCO$_3$ containing 2 mL of water and 1 mL of saturated Na$_2$SO$_3$. The aqueous layer was extracted with Et$_2$O (2×60 mL) and the combined organic layers were dried (MgSO$_4$), filtered and concentrated. The crude product was purified by flash chromatography (2:1 hexanes:ethyl acetate, R$_f$ 0.40) to provide 165 mg (92%) of 23 as an oil.

Reference: Dess, D. B., Martin, J. C. *J. Org. Chem.* 1983, 48, 4155.

The aldehyde 23 (165 mg, 0.294 mmol) was dissolved in 1.5 mL of tert-butyl alcohol containing 2-methyl-2-butene (0.30 mL, 20% v/v) and treated with 0.30 mL of NaH$_2$PO$_4$ buffer (pH 3–4) containing NaClO$_2$ (50 mg, 0.44 mmol). The reaction was complete by TLC analysis after 90 min and was quenched by diluting the reaction with 10:1 Et$_2$O:ethyl acetate to 60 mL followed by drying with Na$_2$SO$_4$. The drying agent was filtered and the filter cake was washed with an additional 80 mL of 10:1 Et$_2$O:ethyl acetate. The solution was concentrated and the resulting crude product purified by flash chromatography (10:1 to 7:1 CH$_2$Cl$_2$: MeOH, R$_f$ 0.42 with 10:1 CH$_2$Cl$_2$:MeOH) to provide 159 mg (95%) of the acid 24 as an oil.

Reference: Kraus, G. A. Roth, B. *J. Org. Chem.* 1980, 45, 4825.

The acid 24 (82 mg, 0.14 mmol) was dissolved in CH$_2$Cl$_2$, cooled to 0° C., treated with diisopropylethyl-amine (75 μL, 0.43 mmol) and pivaloyl chloride (45 μL, 0.37 mmol) sequentially and the cold bath removed. After stirring 2 h at RT, solid tetradecylamine (90 mg, 0.42 mmol) was added and the reaction mixture stirred for 4 h at RT. The reaction was diluted to 50 mL with CH$_2$Cl$_2$, dried (MgSO$_4$), filtered and concentrated. The crude amide was purified by flash chromatography (2:1 to 1:1 hexanes:ethyl acetate, R$_f$ 0.20 with 2:1 hexanes:ethyl acetate) to provide 93 mg (86%) of the amide 26 as an oil.

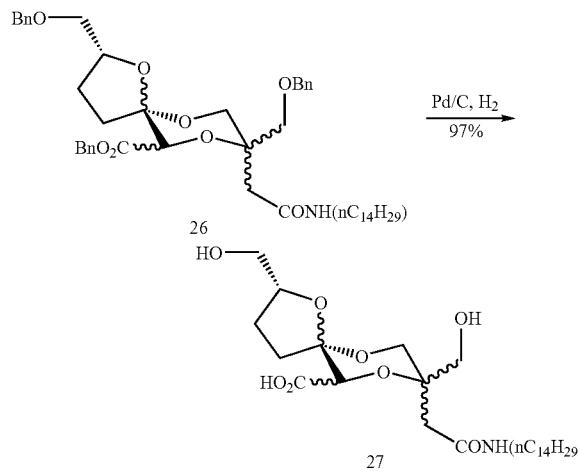

To a 5 mL ethyl acetate solution of the amide 26 (92 mg, 0.12 mmol) was added palladium on carbon (0.12 g, 5% Pd on carbon, 60% water, 23 μmol Pd). The flask was then purged with hydrogen and kept under an atmosphere of hydrogen with a balloon. One major product was detected by TLC analysis (3:1 CH$_2$Cl$_2$:MeOH with 5% v/v water, R$_f$ 0.33) after 2 h at RT. The reaction was diluted with MeOH (25 mL), treated with celite, filtered and the filter cake was washed with 100 mL of MeOH. The solution was concentrated by rotary evaporation and the residue dissolved in 50 mL CHCl$_3$. The solution was dried (Na$_2$SO$_4$), filtered and concentrated. Residual solvents were removed in vacuo (<1 mmHg) to provide 58 mg (97%) of 27 as a light yellow solid.

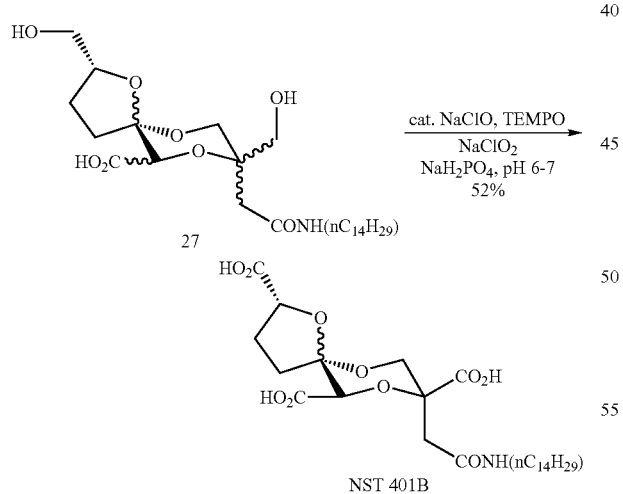

The ketal 27 (30 mg, 59 μmol) was dissolved in 0.6 mL of CH$_3$CN and 0.46 mL of NaH$_2$PO$_4$ buffer (pH 6–7). To this solution was added TEMPO (2 mg, 13 μmol), NaClO$_2$ (28 mg, 248 μmol) and 10 μL of commercial bleach (approximately 4 μmol). After stirring at RT for 24 h, a trace of 27 could be detected by TLC analysis. The reaction was heated to 35° C. for an additional 24 h at which time the reaction was deemed complete by TLC analysis. The reaction mixture was adjusted to pH 9–10 with 10% NaOH and washed with 15 mL of Et$_2$O. The cloudy aqueous layer was then adjusted to pH 1–2 at which time the solution became clear and a white precipitate formed. The solids were insoluble in a variety of organic solvents thus the aqueous layer was simply pipetted off and the solid residue dried in vacuo (<1 mmHg) for 1 h. This treatment provided 16 mg (52%) of NST401-D.

Reference: Zhao, M.; Li, J.; Mano, E.; Song, Z.; Tschaen, D. M.; Grabowski, E. J. J.; Reider, P. J. *J. Org. Chem.* 1999, 64, 2564.

LIST OF ABBREVIATIONS

TBDMSCI tert-butyldimethylsilyl chloride

DMF dimethylformamide

THF tetrahydrofuran

DMSO dimethylsulfoxide

LDA lithium diisopropyl amide

DDQ 2,3-dichloro-5,6-dicyano-1,4-benzoquinone

Et$_2$O diethyl ether

CH$_2$Cl$_2$ dichloromethane

TLC thin layer chromatography

GC gas chromatography

RT room temperature

MgSO$_4$ anhydrous magnesium sulfate

Na$_2$SO$_4$ anhydrous sodium sulfate

PDC pyridinium dichromate

BnBr benzyl bromide

CH$_3$CN acetonitrile

The invention claimed is:

1. A NST 401 compound of formula III:

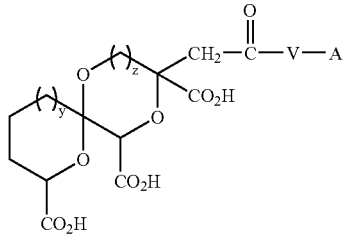

wherein y and z stand each for an integer of 0 or 1; V is —N(H)— or —O—; and wherein A is C$_{14}$H$_{29}$.

2. A NST 401 compound of formula IV:

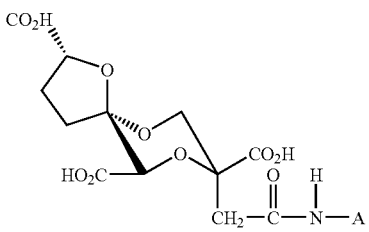

wherein A is C$_{14}$H$_{29}$.

3. A NST 401 compound of formula V:
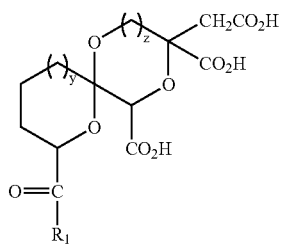
wherein $R_1$ is a —N(H)—$C_{10}H_{29}$ or —O—$C_{14}H_{29}$.
4. A NST 401 compound of formula VI:
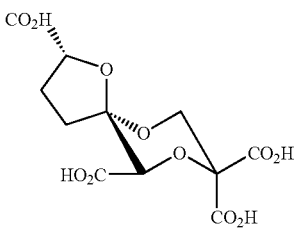
wherein A is $C_{14}H_{29}$.
* * * * *